United States Patent [19]
Pyrozyk et al.

[11] Patent Number: 5,843,047
[45] Date of Patent: Dec. 1, 1998

[54] SYRINGE WITH INTEGRAL SAFETY COVER

[75] Inventors: Ronald Robert Pyrozyk, Penticton; Steve Ronald Sharp, Alberta, both of Canada

[73] Assignee: Okanogan House, Inc., Penticton, Canada

[21] Appl. No.: 790,465

[22] Filed: Jan. 29, 1997

[51] Int. Cl.[6] .................................................. A61M 5/00
[52] U.S. Cl. ............................................ 604/263; 604/192
[58] Field of Search ................................... 604/198, 192, 604/187, 263, 110, 220

[56] References Cited

U.S. PATENT DOCUMENTS

| | | | |
|---|---|---|---|
| 4,826,491 | 5/1989 | Schramm | 604/198 |
| 4,943,282 | 7/1990 | Page et al. | 604/198 |
| 5,057,087 | 10/1991 | Harmon | 604/198 |
| 5,059,185 | 10/1991 | Ryan | 604/263 X |
| 5,116,326 | 5/1992 | Schmidt . | |
| 5,147,303 | 9/1992 | Martin . | |
| 5,207,646 | 5/1993 | Brunel . | |
| 5,222,947 | 6/1993 | D'Amico | 604/198 |
| 5,304,149 | 4/1994 | Morigi | 604/192 |
| 5,328,473 | 7/1994 | Fayngold et al. . | |

FOREIGN PATENT DOCUMENTS 88-03-216.7  9/1988  Germany .

OTHER PUBLICATIONS

Excerpt from RMS Medical Systems Inc. Investment Report; dated Summer 1996; Article title; "Safety Syringes A 'Hot Zone'".
Becton–Dickinson Brochure 1995.
Sketch of Monoject device obtained at a show in New York, Jun. 2, 1997.

*Primary Examiner*—John D. Yasko
*Attorney, Agent, or Firm*—Kolisch Hartwell Dickinson McCormack & Heuser

[57] ABSTRACT

An apparatus and method of covering a needle on a syringe having a barrel and a hypodermic needle connected to the barrel includes the step of extending a telescoping cover engaged with the barrel until the telescoping cover covers the hypodermic needle.

37 Claims, 3 Drawing Sheets

SYRINGE WITH INTEGRAL SAFETY COVER

BACKGROUND OF THE INVENTION

This invention relates to syringes having hypodermic needles and methods and apparatus for covering such needles.

Healthcare workers have become increasingly more aware of the risk of occupational exposure to contaminated blood and other potentially infectious bodily fluids. Needlestick injuries are one of the most common injuries in health care workers. Such injuries appear to be caused by unsafe devices rather than carelessness on the part of the worker. These injuries present the greatest risk of occupational exposure to Human Immunodeficency Virus (HIV) and Hepatitis B.

The prior art includes devices intended to protect against needlestick injuries. Once such device includes a removable cover which is placed over a needle by inserting the needle into the cover while the user holds the cover between the forefinger and the thumb. This, however, presents a risk to the user because if the user misjudges the insertion of the needle into an opening in the cover, the needle may pass the cover and prick the thumb or forefinger. Or, if the user attempts to insert the needle into the cover rapidly, the needle may pierce through a wall of the cover again pricking the thumb or forefinger. These risks result from the necessity to move the needle and cover toward each other during installation of the cover.

Another device known as the RMS retractable syringe, available from RMS Medical Systems Inc. of Vancouver, B.C. Canada, incorporates a metal retaining ring in a tip of a plunger of the syringe. The metal retaining ring locks onto a proximal end portion of a hypodermic needle connected to the syringe, when the plunger is fully depressed into a barrel of the syringe. If the plunger is then drawn outwardly of the barrel, the needle is pulled into the barrel and is automatically canted off-centre so that it cannot be easily forced out of the barrel. Much reliance is placed on the functioning of the metal retaining ring and the act of drawing the plunger from the barrel requires careful attention to how far the plunger is drawn out of the barrel, for if the plunger is drawn too far out, the needle becomes exposed.

The above devices have inherent deficiencies in that with the simple cover device needle prick injuries are reduced only after the cover is in place and installation of the cover presents a great risk in itself. With the RMS device careful manufacturing techniques must be employed to manufacture and assemble the necessary metal and plastic components, with attendant costs. Furthermore, the requirement for careful attention while drawing out the plunger can be a burden to the health care worker using the device.

BRIEF SUMMARY OF THE INVENTION

In accordance with one aspect of the invention, there is provided an apparatus including a barrel having a first end portion for receiving a plunger and a second end portion operable to hold a hypodermic needle and a telescoping cover engaged with the barrel, operable to extend relative to the barrel to cover the hypodermic needle.

Preferably, the apparatus includes a first releasable lock for releasably locking the telescoping cover to the barrel when the telescoping cover is in a non-extended position.

The first releasable lock may include a receptacle in the telescoping cover and a tab on the barrel, the tab being operable to be received in the receptacle.

The telescoping cover may have a wall portion defining the receptacle, and the tab may have a camming portion operable to bear against the wall portion when the telescoping cover is rotated relative to the barrel to disengage the tab with the receptacle thereby unlocking the telescoping cover relative to the barrel and permitting extension of the telescoping cover relative to the barrel.

Preferably, the apparatus includes a second lock for locking the telescoping cover in an extended position fully covering the hypodermic needle.

Preferably, the second lock is operable to permanently lock the telescoping cover in an extended position fully covering the hypodermic needle.

The second lock may include an interfering surface on the barrel and a pawl on the telescoping cover, the pawl being operable to move past the inclined surface when the telescoping cover is extended relative to the barrel and the interfering surface being operable to interfere with movement of the pawl when the telescoping cover is forced in a direction tending to retract the telescoping cover relative to the barrel.

The pawl may have a flexible portion operable to flex radially relative to the telescoping cover.

Preferably, the cover includes a locking member extending axially relative thereto, the pawl being on the locking member.

The apparatus may include an annular portion extending circumferentially around the barrel, the interfering surface being on the annular portion and the cover may include a plurality of pawls operable to move past the annular portion when the telescoping cover is sufficiently extended relative to the barrel to cover the needle, the interfering surface being operable to interfere with movement of the pawls when the telescoping cover is forced in a direction tending to retract the telescoping cover relative to the barrel after the telescoping cover has been sufficiently extended relative to the barrel to cover the needle.

Preferably, the apparatus includes a support for supporting the telescoping cover in an extended position in which the needle is covered.

Preferably, the pawls have respective inclined surfaces and preferably, the support includes an annular ring extending about the barrel, the annular ring having a support surface complementary to the inclined surfaces for mating with the inclined surfaces to support the telescoping cover.

Preferably, the apparatus includes a first releasable lock for releasably locking the telescoping cover to the barrel when the telescoping cover is in a non-extended position and a second lock for locking the telescoping cover in an extended position when the telescoping cover is extended to fully cover the hypodermic needle.

The first releasable lock may include a receptacle on the telescoping cover and a tab on the barrel, the tab being operable to be received in the receptacle when the telescoping cover is in the non-extended position.

Preferably, the second lock includes an annular portion on the barrel and a pawl on the telescoping cover, the pawl being operable to ride over the annular portion when the telescoping cover is extended relative to the barrel and the annular portion being operable to interfere with movement of the pawl when the telescoping cover is forced in a direction tending to retract the telescoping cover relative to the barrel.

Preferably, the pawl has a flexible portion operable to flex radially relative to the telescoping cover.

Preferably, the cover includes a locking member extending axially relative thereto, the pawl being on the locking member.

Preferably, the locking member has a hook spaced apart from the pawl to define the receptacle between the hook and the pawl.

Preferably, the tab has a wedge shape and is dimensioned to be operable to be releasably jammed in the receptacle to secure the telescoping cover to the barrel such that upon rotation of the telescoping cover relative to the barrel, the tab is released from the receptacle, thereby unlocking the telescoping cover relative to the barrel and permitting extension of the telescoping cover relative to the barrel.

Preferably, the telescoping cover has an opening having a shape complementary to the barrel such that the barrel is operable to generally guide the telescoping cover in longitudinal movement relative to the barrel.

Preferably, the telescoping cover has a wall defining an opening through which the hypodermic needle extends, when the telescoping cover is in a non-extended position.

Preferably, the cover is operable to be extended relative to the barrel until at least a portion of the wall is positioned beyond a distal end portion of the hypodermic needle.

Preferably, the apparatus includes a first releasable lock for releasably locking the telescoping cover to the barrel when the telescoping cover is in a non-extended position. The first releasable lock may include a hook on the barrel, the hook defining a receptacle. In addition, the telescoping cover may have a hook which cooperates with the receptacle to lock the telescoping cover to the barrel when the telescoping cover is in a non-extended position.

Preferably, the apparatus includes a second lock for locking the telescoping cover in an extended position fully covering the hypodermic needle, the second lock including a hook ring on the barrel, the hook ring including a radially planar surface and a concentric annular wall defining a receptacle.

Preferably, the second lock further includes at least one resiliently deformable hook on the cover, the hook having a barb having an inclined surface and a radially planar surface, the barb being operable to resiliently deform as it is forced into the receptacle formed between the radially planar surface of the hook ring and the annular wall of the hook ring until the radially planar surfaces abut each other. In this position, the radially planar surface on the hook ring interferes with the radially planar surface on the hook and prevents counter movement of the telescoping cover in a direction tending to retract the telescoping cover relative to the barrel.

Preferably, the apparatus includes a support for supporting the telescoping cover in an extended position in which the needle is covered. To facilitate this the telescoping cover may have an inside surface complementary to the shape of the concentric annular wall such that the concentric annular wall acts as a support surface for supporting the telescoping cover in an extended position in which the needle is covered.

Preferably, the barrel has an outer surface and preferably, the telescoping cover has a plurality of hooks having respective axially extending walls positioned on the cover such that the axially extending walls ride on the outer surface of the barrel while the inside surface of the telescoping cover rides on the annular concentric wall of the hook ring as the telescoping cover is telescopically extended.

In accordance with another aspect of the invention, there is provided a method of covering a needle on a syringe having a barrel and a hypodermic needle connected to the barrel. The method includes the step of extending a telescoping cover engaged with the barrel until the telescoping cover covers the hypodermic needle.

Preferably, the method also includes the step of locking the telescoping cover in an extended position when the telescoping cover is extended to fully cover the hypodermic needle and preferably, the telescoping cover is permanently locked in an extended position when the telescoping cover is extended to fully cover the hypodermic needle.

The telescoping cover may be releasably locked to the barrel when the telescoping cover is in a non-extended position and preferably, the telescoping cover is released from the barrel to permit extension of the telescoping cover relative to the barrel, by rotating the telescoping cover relative to the barrel.

Preferably, the telescoping cover portion is supported while the telescoping cover covers the needle.

In accordance with another aspect of the invention, there is provided a syringe including a barrel having a first and second opposite end portions, a plunger operable to be received in the first end portion, a hypodermic needle connected to the second end portion and a telescoping cover engaged with the barrel, operable to extend relative to the barrel to extend beyond the second end portion to cover the hypodermic needle.

In accordance with another aspect of the invention, there is provided a method of covering a hypodermic needle on a syringe. The method includes the steps of supporting a cover in a first position, about a barrel of the syringe, moving the cover longitudinally relative to the barrel until the cover extends about the hypodermic needle.

BRIEF DESCRIPTION OF THE SEVERAL VIEWS OF THE DRAWING

In drawings which illustrate embodiments of the invention.

DETAILED DESCRIPTION OF THE INVENTION

Figure 1:
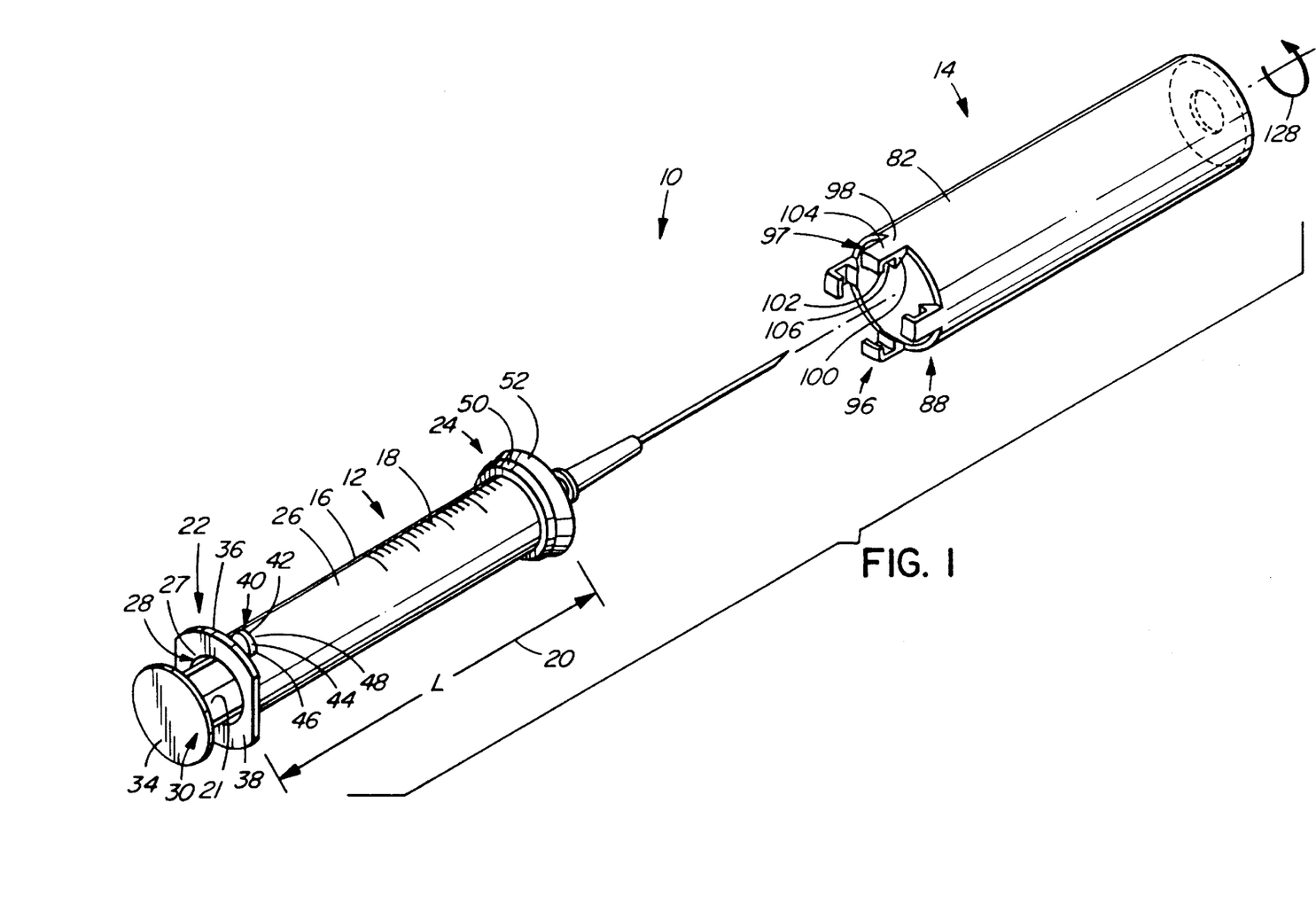
FIG. 1 is a an oblique exploded view of an apparatus according to a first embodiment of the invention.

Referring to FIG. 1, an apparatus according to a first embodiment of the invention is shown generally at 10. The apparatus includes a syringe shown generally at 12 and a telescoping cover 14 formed over the syringe as explained below.

Barrel

The syringe includes an elongated cylindrical barrel 16 formed of transparent or clear plastic having a plurality of graduations 18 and first length 20. The barrel 16 has first and second end portions 22 and 24 and an outer cylindrical surface 26 extending between the end portions. The first end portion 22 has wall 27 defining a circularly shaped plunger hole extending through the barrel 16 and having an opening 28 for receiving an elongated plunger shown generally at 30. The plunger 30 has a shaft 21 operable to be received in the plunger opening 28 and has a thumb-actuated pressure pad 34 which enables a user to press the plunger 30 into the plunger opening 28 to pressurize fluid within the plunger hole.

The first end portion 22 also has first and second finger grip tabs 36 and 38 extending radially outwardly of the plunger opening 28 to enable a user to grasp the first end portion 22. Thus, the user is able to grasp the finger grip tabs 36 and 38 with the forefinger and middle finger and actuate the plunger 30 with the thumb.

The first end portion 22 further has a radially extending wedge-shaped tab 40 disposed on the outer cylindrical surface 26, in spaced apart relation from the first finger grip tab 36. The wedge shaped tab 40 extends radially from the outer surface and has a camming portion 42 having first, second and third camming surfaces 44, 46 and 48.

Figure 2:
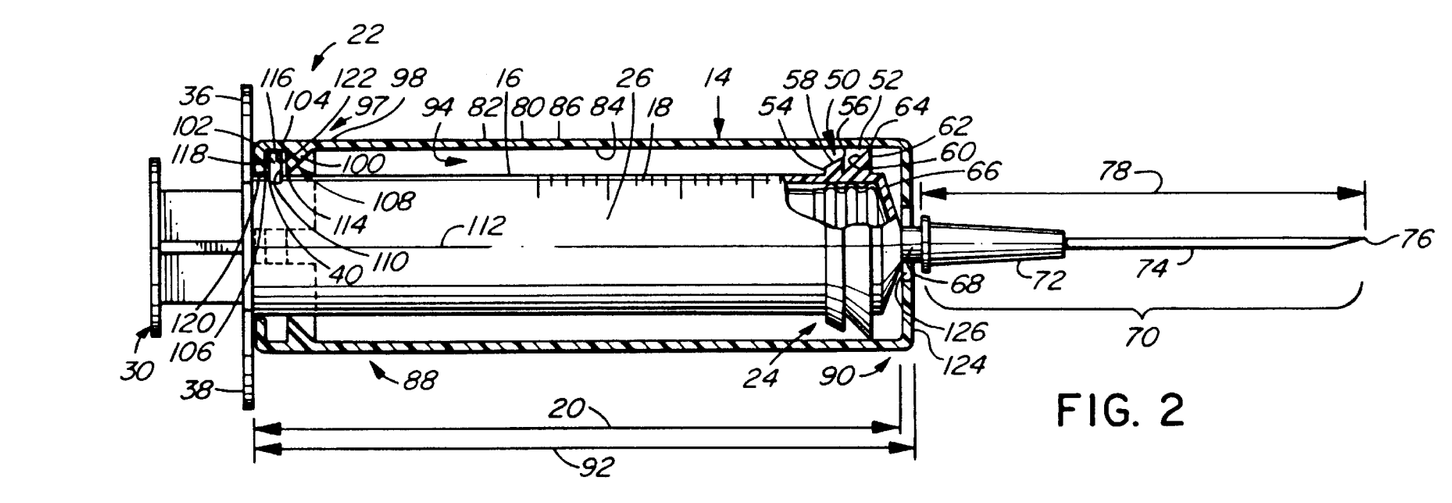
FIG. 2 is a fragmented cross-sectional view of the apparatus of FIG. 1, in a position ready for use.

The second end portion 24 has first and second concentric annular portions 50 and 52 which extend about the barrel 16. Referring to FIG. 2, the first concentric annular portion 50 has first and second radially planar surfaces 54 and 56 and an inclined surface 58 extending between the first and second radially planar surfaces 54 and 56. This inclined surface 58 thus extends at an obtuse angle relative to the first inclined surface 58 and extends at an acute angle relative to the second radially planar surface 56. In this embodiment, the obtuse angle is approximately 120 degrees.

The second concentric annular portion 52 has a second inclined surface 60 and a third radially planar surface 62. The second inclined surface 60 extends from the second radially planar surface 56 at an acute angle of approximately 45 degrees and the third radially planar surface 65 extends in a radial plane at a most distal position on the barrel 16. The second inclined surface 60 and the third radially planar surface 62 thus form a first apex 64 projecting radially outwardly of the barrel 16.

The barrel 16 is terminated in a truncated conical end 66 having a slightly tapered conduit 68. A hypodermic needle assembly 70 includes a needle fastener 72 and a needle 74 having a needle point 76. The needle 74 is connected to the needle fastener 72 and the needle fastener 72 is secured to the slightly tapered conduit 68 by a friction-fit, in the convention manner. The needle assembly 70 has an overall length 78 less than the length 20 of the barrel.

It will be appreciated therefore that it may be said that the apparatus includes a barrel 16 having a first end portion 22 for receiving a plunger 30 and a second end portion 24 operable to hold a hypodermic needle 74.

Telescoping cover

Still referring to FIG. 2, the barrel 16 and telescoping cover 14 are formed together using a multiphase injection moulding process. The telescoping cover 14 is formed as a generally elongated tube 80 defined by a cylindrical wall 82 of transparent plastic so that the graduations 18 on the barrel 16 can be seen through the telescoping cover 14. The cylindrical wall 82 has inside and outside surfaces 84 and 86 and first and second end portions 88 and 90 and has a length 92 slightly greater than the length 20 of the barrel 16. The inside surface 84 defines a hole 94 in the tube 80 in which the barrel 16 is received, the hole having a shape generally complementary to the shape of the outer surface 26 of the barrel 16, which, in this embodiment is circularly cylindrical.

Referring to FIG. 1, a plurality of locking members 96 are formed diametrically opposite each other and extend axially relative to the cylindrical wall 82 at the first end portion 88 thereof. Each locking member 97 includes a flexible portion 98, a pawl 100 and a hook 102. The flexible portion 98 connects the pawl 100 to the cylindrical wall 82 and has sufficient resilience to allow the pawl 100 to have a little movement radially outwardly and to return the pawl 100 to its original position after such movement. The hook 102 is disposed most distal to the cylindrical wall 82 and the pawl 100 and hook 102 are spaced apart axially by a connecting wall 104. A receptacle 106 is defined between the pawl 100 and the hook 102. The locking member 97 thus has a hook 102 spaced apart from the pawl 100 to define a receptacle 106 between the hook and the pawl.

Referring to FIG. 2, the pawl 100 has an inclined surface 108 and a radially planar surface 110. The inclined surface 108 extends at an angle of approximately 45 degrees relative to the axis 112 of the cylindrical wall 82. The radially planar surface 110 is disposed more distal to the cylindrical wall 82 than the inclined surface 108 and extends from the inclined surface 108 in a radial plane relative to the axis 112. The radially planar surface 110 and inclined surface 108 thus form a second apex 114 disposed radially inwardly of the inside surface 84.

The hook 102 has first and second radially planar surfaces 116 and 118 which extend in respective spaced apart radial planes. An axially parallel surface 120 extends between the first and second radially planar surfaces 116 and 118 at a distance such that the axially parallel surface 120 is coplanar with the second apex 114.

The connection wall 104 has an inside surface 122 extending between the radially planar surface 110 of the pawl 100 and the first radially planar surface 116 of the hook 102. The receptacle 106 is thus defined by the radially planar surface 110 of the pawl 100, the inside surface 122 of the connecting wall 104 and the first radially planar surface 116 of the hook 102. These surfaces are dimensioned and positioned on the locking member 97 such that the tab 40 is operable to be snugly received in the receptacle 106. The pawl 100, connecting wall 104 and hook 102 are contiguous with the cylindrical wall 82 and thus the respective surfaces of these components act as a wall portion defining the receptacle 106.

The second end portion 90 of the telescoping cover includes a generally disk-shaped end wall 124 extending in a radial plane relative to the cylindrical wall 82 and terminating the cylindrical wall. The end wall 124 has a central opening 126 therein, shown in broken outline, for receiving the needle assembly 70 therethrough. Preferably, the central opening 126 is dimensioned to have a diameter slightly greater than the diameter of the needle fastener so that the central opening 126 is of minimal size.

Operation

Referring to FIG. 2, the apparatus is shown in a position ready for use. In this position, the telescoping cover 14 is in a non-extended or retracted position relative to the barrel 16 and the tab 40 is received in the receptacle such that the first, second and third camming surfaces 44, 46 and 48 are tightly received against the radially planar surface 110 of the pawl 100, the inside surface 122 of the connecting wall 104 and the first radially planar surface 116 of the hook 102. In this position, the telescoping cover 14 is releasably locked to the barrel 16. It will therefore be appreciated that the receptacle 106 on the telescoping cover 14 and the tab 40 on the barrel 16 act as a first releasable lock for releasably locking the telescoping cover 14 to the barrel 16 when the telescoping cover 14 is in a non-extended position.

It will be appreciated that syringes are provided separately from the needle assembly 70 and that the needle assembly 70 is removed from a separate package and fastened to the barrel 16 by placing the needle fastener 72 over the slightly tapered conduit 68, whereby the needle assembly is held thereon by a friction-fit. The slightly tapered conduit 68 extends through the central opening 126 in the end wall 124 to facilitate fastening of the needle assembly 70. Thus, the telescoping cover 14 has a wall 124 defining an opening 126 through which the hypodermic needle extends 74, when the telescoping cover 14 is in a non-extended position.

The syringe 12 is then used in the conventional manner to inject medication into a patient or to draw fluid from the patient.

After use of the syringe 12, the outer surface 86 of the telescoping cover 14 is gripped with one hand while the finger grip tabs 36 and 38 are grasped by the other hand and the telescoping cover 14 is rotated relative to the barrel 16 in the direction of arrow 128 shown in FIG. 1. Referring to FIG. 2, such rotation releases the tab 40 from the receptacle 106 allowing the telescoping cover 14 to be positioned such that the tab 40 is between adjacent locking members (97), whereupon the telescoping cover 14 may be telescopically extended relative to the barrel 16. The tab 40 is thus releasably jammed in the receptacle 106 to secure the telescoping cover 14 to the barrel 16 until the telescoping cover 14 is rotated relative to the barrel 16 to release the tab 40 from the receptacle 106, thereby unlocking the telescoping cover 14 relative to the barrel 16 and permitting extension of the telescoping cover 14 relative to the barrel 16.

The outer surface 26 of the barrel 16 and the hole 94 in the tubular telescoping cover 14 having a shape generally complementary to the shape of the cylindrical surface 26 of the barrel 16 acts to guide the telescoping cover 14 in axial movement relative to the barrel 16 as the telescoping cover 14 is extended relative to the barrel 16. Guiding of the telescoping cover 14 is enhanced by the apex 114 of the pawl and the axially parallel surface 120 of the hook 102 riding on the outer surface 26 of the barrel 16 and by the inside surface 84 of the telescoping cover 14 riding on the apex 64 of the second annular portion 52 as the telescoping cover 14 is extended relative to the barrel 16.

When the telescoping cover 14 has been extended sufficiently, the pawl 100 will come in contact with the first annular portion 50. Further axial movement of the telescoping cover 14 causes the inclined surface 108 on the pawl 100 to be pushed radially outwardly by the first inclined surface 58 on the first annular portion 50 as the inclined surface 108 on the pawl 100 rides over the inclined surface 58 on the first annular portion 50.

Figure 3:
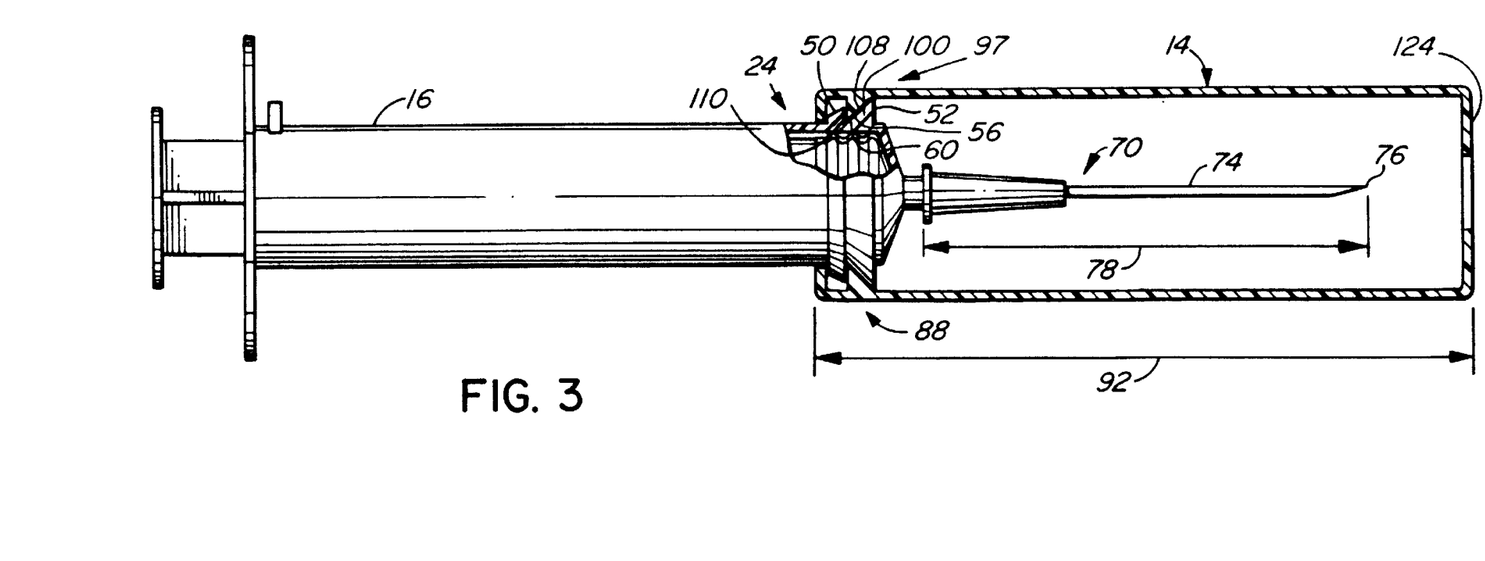
FIG. 3 is a fragmented cross-sectional view of the apparatus of FIG. 1, with a cover thereof shown in a position in which a needle connected to the apparatus is covered.

When the apex 114 of the pawl 100 clears the second radially planar surface 56 of the first annular portion 50, the resilience of the flexible portion 98 returns the pawl 100 to its original position, whereupon the inclined surface 108 on the pawl 100 contacts the inclined surface 60 on the second annular portion 52 and the radially planar surface 110 on the pawl 100 abuts the second radially planar surface 56 of the first annular portion 50 as shown in FIG. 3. In this position, the second radially planar surface 56 of the first annular portion 50 interferes with the radially planar surface 110 on the pawl 100 and prevents counter movement of the telescoping cover 14 in a direction tending to retract the telescoping cover 14 relative to the barrel 16. In this position, because the locking members (97) are located at the first end portion 88 of the telescoping cover 14 and because the first and second annular portions 50 and 52 are located at the second end portion 24 of the barrel 16, the telescoping cover 14 is fully extended relative to the barrel 16. When the telescoping cover 14 portion is fully extended in this manner, because the length 92 of the telescoping cover 14 is greater than the length 78 of the needle assembly 70, the end wall 124 is positioned beyond the needle point 76 of the hypodermic needle 74, whereupon the needle is fully covered and the user is guarded against needle prick injuries. Thus, it may be said that the apparatus includes a telescoping cover 14 engaged with the barrel 16, operable to extend relative to the barrel 16 to cover the hypodermic needle 74.

The user cannot retract the telescoping cover 14 relative to the barrel 16 due to the interference between the radially planar surface 110 on the pawl 100 and the radially planar surface 56 on the first annular portion 50. The second radially planar surface 56 on the first annular portion 50 thus acts as an interfering surface operable to interfere with movement of the pawl 100 when the telescoping cover 14 is forced in a direction tending to retract the telescoping cover 14 relative to the barrel 16 after the telescoping cover has been sufficiently extended relative to the barrel 16 to cover the needle 74. The pawl 100 and the first annular portion 50 thus act as a second lock for permanently locking the telescoping cover 14 in an extended position when the telescoping cover 14 is in an extended position fully covering the needle 74.

The telescoping cover 14 is supported in the extended position by the mating of the inclined surfaces 60 and 108 on the pawl 100 and the second annular portion 52 and by the mating of the second annular surface 56 with the radially planar surface 110 on the pawl 100. Axial movement is prevented by the inclined surfaces 60 and 108 mating with each other and by the interference between the second radially planar surface 56 and the radially planar surface 110 on the pawl 100. Radial movement is prevented by the pawls 100 being disposed on diametrically opposite sides of the telescoping cover 14. Thus, the inclined surface 60 of the second annular portion 52 acts as a support surface complementary to the inclined surfaces 108 on the pawls 100 for mating with the inclined surfaces 108 on the pawls 100 to support the telescoping cover 14 in an extended position in which the needle 74 is covered.

Second Embodiment

Figure 4:
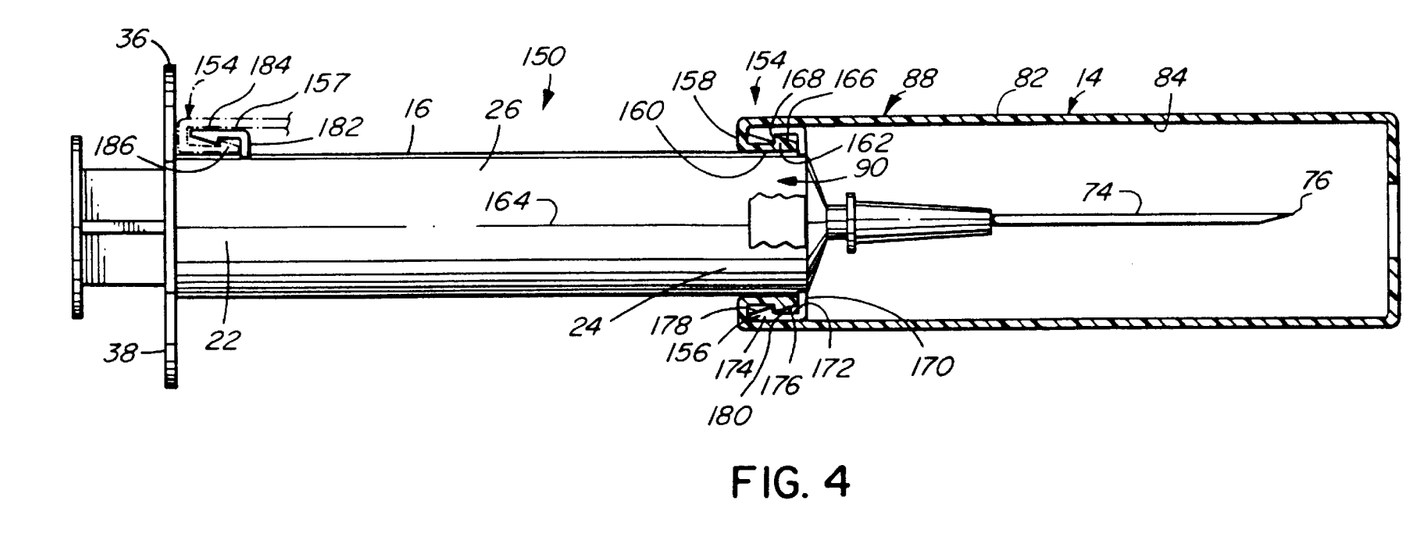
FIG. 4 is a fragmented cross-sectional view of an apparatus according to a second embodiment of the invention.

Referring to FIG. 4, an apparatus according to a second embodiment of the invention is shown generally at 150. The apparatus includes a telescoping cover 14 and barrel 16 having components similar to that as shown in the first embodiment, which are designated by the same numerical references used in the description of the apparatus according to the first embodiment.

The apparatus according to the second embodiment differs from the apparatus according to the first embodiment in that in place of the locking members, the apparatus according to the second embodiment includes a plurality of hooks 154 disposed on diametrically opposite locations around the first end portion 88 of the cylindrical wall 82, a mating hook ring 156 is formed on the second end portion 90 of the barrel 16 and a hook 157 is formed on the first end portion 22 of the barrel 16.

The hooks 154 on the telescoping cover include a radially inwardly extending wall 158, an axially parallel wall 160 and a barb 162. The radially inwardly extending wall 158 extends radially inwardly from the cylindrical wall 82. The axially parallel wall 160 extends parallel to the axis 164 a short distance and the barb 162 terminates the axially parallel wall 160. The barb 162 has an inclined surface 166 and a radially planar surface 168. The inclined surface 166 extends outwardly toward the axially parallel wall 160 and the radially planar surface 168 extends radially inward from the inclined surface 166.

The hook ring 156 extends about the second end portion 24 of the barrel 16 and has a radially outwardly extending annular wall 170, a concentric annular wall 172 concentric with the barrel 16 and a lip 174 terminating the circular wall. The lip 174 has an inclined surface 176 converging toward the second end portion 24 of the barrel 16 and terminated in a radially planar surface 178 extending radially outwardly of the inclined surface 176.

An annular receptacle 180 is thus formed between the radially planar surface 178 of the hook ring 156 and the annular wall 170 of the hook ring. The annular wall 170 of the hook ring 156 and the radially extending walls 158 of the hooks 154 are dimensioned such that the barbs 162 are operable to be snugly received between the concentric annular wall 172 and the outer surface 26 of the barrel 16 and between the radially outwardly extending annular wall 170 and the radially planar surface 178 on the hook ring 156.

Figure 5:
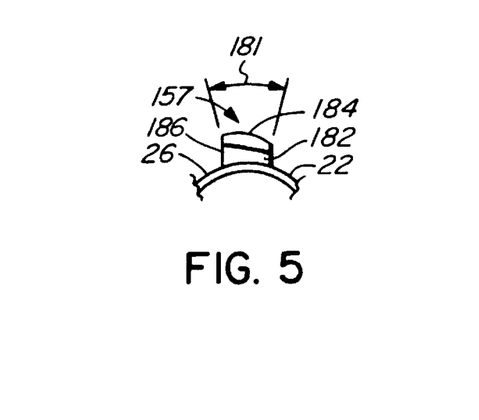
FIG. 5 is a fragmented end view of the apparatus shown in FIG. 4.

The hook 157 on the first end portion 22 has a shape similar to that of the hook ring 156 at the second end portion 24 with the exception that the hook 157 on the first end portion 22 is arcuate and extends through an angle 181 of approximately 10 degrees, seen best in FIG. 5. The hook includes a radially extending wall 182 and an axially parallel wall 184. The radially extending wall 182 serves to space the axially parallel wall 184 from the outer surface 26 of the barrel 16 to form an arcuate wedge-shaped receptacle 186 operable to receive and grip one of the hooks 154 formed in the telescoping covers.

Operation

Referring to FIG. 4, a retracted position of the cover 17, wherein the apparatus is ready for use is shown in fragmented, broken outline. In this position, the telescoping cover 14 is in a non-extended position relative to the barrel 16 and one of the hooks 154 is received in the receptacle 186 such that the hook is tightly received against the axially extending wall 182 of the hook on the barrel 16. In this position, the telescoping cover is releasably locked to the barrel. It will therefore be appreciated that the receptacle 186 formed by the hook 157 on the barrel 16 and the hook 154 on the telescoping cover 14 act as a first releasable lock for releasably locking the telescoping cover 14 to the barrel 16 when the telescoping cover 14 is in a non-extended position.

After use of the syringe, the outer surface 26 of the telescoping cover 14 is gripped with one hand while the finger grip tabs are 36 and 38 grasped by the other hand and the telescoping cover 14 is rotated relative to the barrel 16 to release the hook 154 from the receptacle 186. The telescoping cover may then be positioned such that the barrel hook 157 is between adjacent hooks 154, whereupon the telescoping cover 14 may be telescopically extended relative to the barrel 16. The hook 154 is thus releasably jammed in the receptacle 186 to secure the telescoping cover 14 to the barrel 16 until the telescoping cover 14 is rotated relative to the barrel 16 to release the hook 154 from the receptacle 186, thereby unlocking the telescoping cover 14 relative to the barrel 16 and permitting extension of the telescoping cover 14 relative to the barrel 16.

Guiding of the telescoping cover 14 is enhanced by the axially extending walls 160 of the hooks 154 riding on the outer surface 26 of the barrel 16, while the inside surface 84 of the telescoping cover 14 rides on the annular concentric wall 172 of the hook ring 156.

When the telescoping cover 14 has been extended sufficiently, the inclined surfaces 176 and 166 of the hook ring 156 and the hooks 154 engage and resiliently deform as the barbs 162 of the hooks 154 are forced into the receptacle 180 formed between the radially planar surface 178 of the hook ring and the annular wall 170 of the hook ring 156.

In this position, the radially planar surfaces 178 and 168 abut each other whereupon the radially planar surface 178 on the hook ring 156 interferes with the radially planar surface 168 on the hooks 154 and prevents counter movement of the telescoping cover 14 in a direction tending to retract the telescoping cover 14 relative to the barrel 16. In this position, the telescoping cover 14 is fully extended relative to the barrel. When the telescoping cover is fully extended in this manner, because the length of the telescoping cover is greater than the length of the needle assembly, the needle is fully covered and the user is guarded against needle prick injuries. Furthermore, the user cannot retract the telescoping cover 14 relative to the barrel 16. The hook ring 156 and the hooks 154 thus act as a second lock for permanently locking the telescoping cover 14 in an extended position when the telescoping cover 14 is in an extended position fully covering the needle 74.

The telescoping cover 25 is supported in the extended position by the mating of the inside surface 84 of the telescoping cover 14 with the concentric annular wall 172 of the hook ring 156 and the tight grip on the hooks 154 provided by the hook ring 156. Thus, the concentric annular wall 172 of the hook ring 156 acts as a support surface for supporting the telescoping cover 14 in an extended position in which the needle 74 is covered.

It is a particular advantage of the invention that after the use of the syringe, the telescoping cover 14 may simply and quickly be rotated relative to the barrel 16 and drawn outwardly of the barrel 16, or telescopically extended relative to the barrel 16, in a direction away from the point 76 of the needle 74 until the needle is covered. Thus, the user's hands are kept away from the needle point 76 and there is no movement which would drive the needle 74 into the user's hand or body. Rather, all movement is away from the needle point 76. Thus, the operation of the apparatus presents little risk to the user and after operation of the device the risk of needle prick injuries is small as needle 74 is completely covered.

While specific embodiments of the invention have been described and illustrated, such embodiments should be considered illustrative of the invention only and not as limiting the invention as construed in accordance with the accompanying claims.

What is claimed is:

1. An apparatus comprising:
   a) a barrel having a first end portion for receiving a plunger and a second end portion operable to hold a hypodermic needle;
   b) a telescoping cover engaged with the barrel, the cover being operable to extend axially relative to said barrel to cover the hypodermic needle, and operable to be selectively rotatable relative to said barrel, and
   c) a first releasable lock cooperating with said telescoping cover and said barrel for releasably locking said telescoping cover to said barrel when said telescoping cover is in a retracted position, the first releasable lock including a receptacle and a tab; the tab being operable to be releasably jammed in said receptacle to lock said cover relative to said barrel to prevent said axial extension of said cover, and being operable to be removable from the receptacle to unlock said telescoping cover relative to said barrel following relative rotation between said cover and said barrel to permit said axial extension of said telescoping cover relative to said barrel.

2. An apparatus as claimed in claim 1 further including a second lock for locking said telescoping cover in an extended position fully covering the hypodermic needle.

3. An apparatus as claimed in claim 2 wherein said second lock is operable to permanently lock said telescoping cover in an extended position fully covering the hypodermic needle.

4. An apparatus as claimed in claim 3 wherein said second lock includes an interfering surface on said barrel and a pawl on said telescoping cover, said pawl being operable to move past said inclined surface when said telescoping cover is extended relative to said barrel and said interfering surface being operable to interfere with movement of said pawl when said telescoping cover is forced in a direction tending to retract said telescoping cover relative to said barrel.

5. An apparatus as claimed in claim 4 wherein said pawl has a flexible portion operable to flex radially relative to said telescoping cover.

6. An apparatus as claimed in claim 5 wherein said cover includes a locking member extending axially relative thereto, said pawl being on said locking member.

7. An apparatus as claimed in claim 4 further including an annular portion extending circumferentially around said barrel, said interfering surface being on said annular portion and wherein said cover includes a plurality of pawls operable to move past said annular portion when said telescoping cover is sufficiently extended relative to said barrel to cover the needle, said interfering surface being operable to interfere with movement of said pawls when said telescoping cover is forced in a direction tending to retract said telescoping cover relative to said barrel after said telescoping cover has been sufficiently extended relative to said barrel to cover the needle.

8. An apparatus as claimed in claim 7 further including a support for supporting said telescoping cover in an extended position in which the needle is covered.

9. An apparatus as claimed in claim 8 wherein said pawls have respective inclined surfaces and wherein said support includes an annular ring extending about said barrel, said annular ring having a support surface complementary to said inclined surfaces for mating with said inclined surfaces to support said telescoping cover.

10. An apparatus as claimed in claim 1 further including:
a) a first releasable lock for releasably locking said telescoping cover to said barrel when said telescoping cover is in a non-extended position; and
b) a second lock for locking said telescoping cover in an extended position when said telescoping cover is extended to fully cover the hypodermic needle.

11. An apparatus as claimed in claim 10 wherein said first releasable lock includes a receptacle on said telescoping cover and a tab on said barrel, said tab being operable to be received in said receptacle when said telescoping cover is in said non-extended position.

12. An apparatus as claimed in claim 11 wherein said second lock includes an annular portion on said barrel and a pawl on said telescoping cover, said pawl being operable to ride over said annular portion when said telescoping cover is extended relative to said barrel and said annular portion being operable to interfere with movement of said pawl when said telescoping cover is forced in a direction tending to retract said telescoping cover relative to said barrel.

13. An apparatus as claimed in claim 12 wherein said pawl has a flexible portion operable to flex radially relative to said telescoping cover.

14. An apparatus as claimed in claim 13 wherein said cover includes a member extending axially relative thereto, said pawl being on said locking member.

15. An apparatus as claimed in claim 14 wherein said locking member has a hook spaced apart from said pawl to define said receptacle between said hook and said pawl.

16. An apparatus as claimed in claim 15 wherein said tab has a wedge shape and is dimensioned to be operable to be releasably jammed in said receptacle to secure said telescoping cover to said barrel such that upon rotation of said telescoping cover relative to said barrel, said tab is released from said receptacle, thereby unlocking said telescoping cover relative to said barrel and permitting extension of said telescoping cover relative to said barrel.

17. An apparatus as claimed in claim 16 further including a support for supporting said telescoping cover in an extended position in which the needle is covered.

18. An apparatus as claimed in claim 17 wherein said pawls have respective inclined surfaces and wherein said support includes an annular ring extending about said barrel, said annular ring having a support surface complementary to said inclined surfaces for mating with said inclined surfaces to support said telescoping cover.

19. An apparatus as claimed in claim 1 wherein said telescoping cover has an opening having a shape complementary to said barrel such that said barrel is operable to generally guide said telescoping cover in longitudinal movement relative to said barrel.

20. An apparatus as claimed in claim 1 wherein said telescoping cover has a wall defining an opening through which the hypodermic needle extends, when said telescoping cover is in a non-extended position.

21. An apparatus as claimed in claim 20 wherein said cover is operable to be extended relative to said barrel until at least a portion of said wall is positioned beyond a distal end portion of the hypodermic needle.

22. An apparatus as claimed in claim 1 further including a first releasable lock for releasably locking said telescoping cover to said barrel when said telescoping cover is in a non-extended position, said first releasable lock including a hook on said barrel, said hook defining a receptacle and wherein the telescoping cover has a hook which cooperates with the receptacle to lock the telescoping cover to the barrel when the telescoping cover is in a non-extended position.

23. An apparatus as claimed in claim 22 further including a second lock for locking said telescoping cover in an extended position fully covering the hypodermic needle, wherein said second lock includes a hook ring on said barrel, said hook ring including a radially planar surface and a concentric annular wall defining a receptacle.

24. An apparatus as claimed in claim 23 wherein said second lock includes at least one resiliently deformable hook on said cover, said hook having a barb having an inclined surface and a radially planar surface, said barb being operable to resiliently deform as it is forced into the receptacle formed between the radially planar surface of the hook ring and the annular wall of the hook ring until said radially planar surfaces abut each other whereupon the radially planar surface on the hook ring interferes with the radially planar surface on the hook and prevents counter movement of the telescoping cover in a direction tending to retract the telescoping cover relative to the barrel.

25. An apparatus as claimed in claim 24 further including a support for supporting said telescoping cover in an extended position in which the needle is covered.

26. An apparatus as claimed in claim 25 wherein said telescoping cover has an inside surface complementary to the shape of said concentric annular wall such that said concentric annular wall acts as a support surface for supporting the telescoping cover in an extended position in which the needle is covered.

27. An apparatus as claimed in claim 26 wherein said barrel has an outer surface and wherein said telescoping cover has a plurality of hooks having respective axially extending walls positioned on said cover such that said axially extending walls ride on said outer surface of the barrel while the inside surface of the telescoping cover rides on the annular concentric wall of the hook ring as said telescoping cover is telescopically extended.

28. A method of covering a needle on a syringe having a barrel and a hypodermic needle connected to the barrel, the method comprising the steps of:

a) rotating a telescoping cover releasably jammed in engagement with said barrel to release said telescoping cover from the barrel, and b) extending the telescoping cover relative to the barrel until the telescoping cover covers the hypodermic needle to protect the needle.

29. A method as claimed in claim 28 further including the step of locking said telescoping cover in an extended position when said telescoping cover is extended to fully cover the hypodermic needle.

30. A method as claimed in claim 28 further including the step of permanently locking said telescoping cover in the extended position when said telescoping cover is extended to fully cover the hypodermic needle.

31. A method as claimed in claim 28 further including the step of rotating said telescoping cover relative to the barrel to release said telescoping cover from the barrel to permit extension of said telescoping cover relative to the barrel.

32. A method as claimed in claim 28 further including the step of supporting said telescoping cover while said telescoping cover covers the needle.

33. A syringe comprising:

a) a barrel having first and second opposite end portions;

b) a plunger operable to be received in said first end portion;

c) a hypodermic needle connected to said second end portion;

d) a telescoping cover engaged with said barrel, the cover being operable to extend axially relative to said barrel to extend beyond said second end portion to cover said hypodermic needle, and operable to be selectively rotatable relative to said barrel, and e) a first releasable lock cooperating with said telescoping cover and said barrel for releasably locking said telescoping cover to said barrel when said telescoping cover is in a retracted position, the first releasable lock including a receptacle and a tab; the tab being operable to be releasably jammed in said receptacle to lock said cover relative to said barrel to prevent said axial extension of said cover, and being selectively removable from the receptacle to unlock said telescoping cover relative to said barrel following relative rotation between said cover and said barrel to permit said axial extension of said telescoping cover relative to said barrel.

34. An apparatus as claimed in claim 1 in which:

a) said receptacle has a wall portion, and b) said tab has a camming portion operable to bear against said wall portion when said telescoping cover is rotated relative to said barrel to engage and disengage said tab with said receptacle to permit locking and unlocking of said cover with respect to the barrel.

35. An apparatus is claimed in claim 1 in which:

a) the telescoping cover has the receptacle of the first releasable lock, and b) the barrel has the tab of the first releasable lock.

36. An apparatus as claimed in claim 1 in which:

a) the tab of the first releasable lock engages the receptacle following relative rotation in one direction, and is removable therefrom following relative rotation in an opposite direction.

37. An apparatus as claimed in claim 34 in which:

a) the telescoping cover has the receptacle of the first releasable lock, and b) the barrel has the tab of the first releasable lock.

* * * * *